United States Patent [19]

Meckler

[11] Patent Number: 4,468,103

[45] Date of Patent: Aug. 28, 1984

[54] EYE MEDICATION DISPENSING FRAMES AND INSERT

[76] Inventor: Milton Meckler, 16348 Tupper St., Sepulveda, Calif. 91343

[21] Appl. No.: 335,068

[22] Filed: Dec. 28, 1981

[51] Int. Cl.$^3$ .......................... G02C 1/00; A61M 1/00
[52] U.S. Cl. ..................................... 351/158; 351/41; 604/300
[58] Field of Search ................... 351/158, 41; 604/300, 604/301, 302

[56] References Cited

U.S. PATENT DOCUMENTS 2,600,920  6/1952  Raschkind ........................... 128/249
3,446,209  5/1969  Macha .............................. 351/158 X
4,183,355  1/1980  Meckler ............................. 128/233

Primary Examiner—Rodney B. Bovernick
Attorney, Agent, or Firm—William H. Maxwell

[57] ABSTRACT

A frame and sterile sleeve and eyedropper combination in kit form for therapeutic self-administration of medication to the eyes and comprised of an eyeglass frame with omni positionable guides slidable through lens openings and with bores therethrough for the reception of sterile sleeves and with guide-adjustment-lock means for the selective positioning of said guides, the sleeves being expendible tubular elements adapted to receive and position the eyedropper, and the guides having a peripheral target focused upon by the eye to expose a portion of the conjunctiva.

16 Claims, 9 Drawing Figures

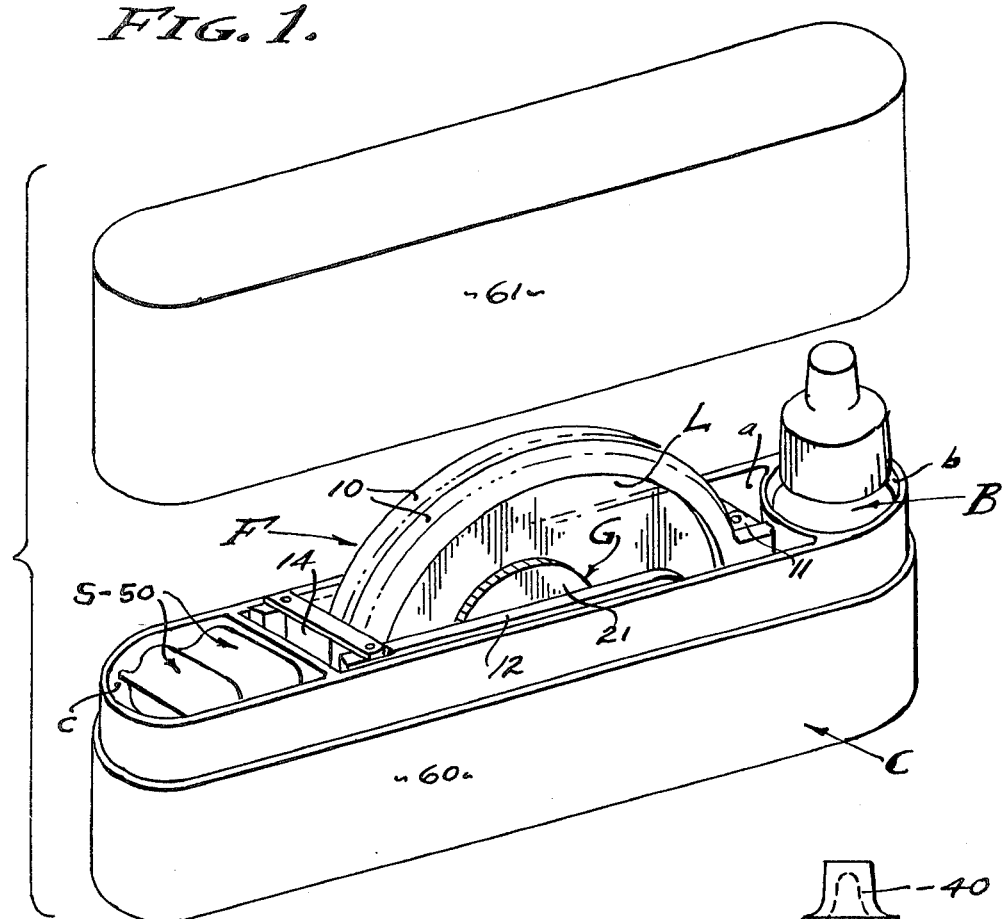

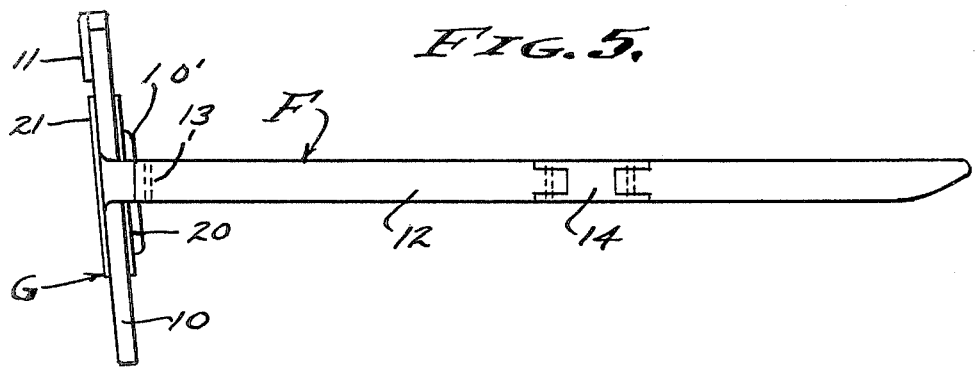
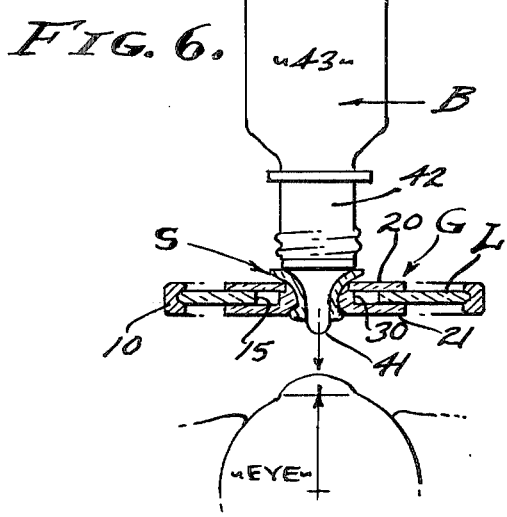
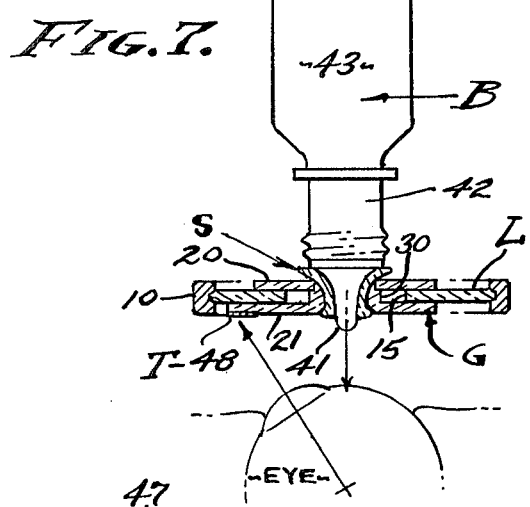
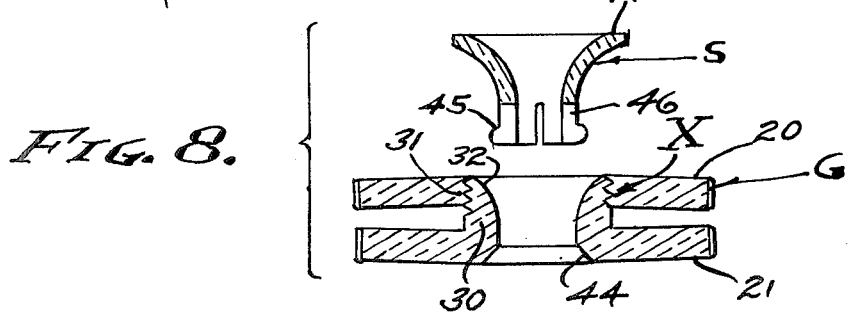
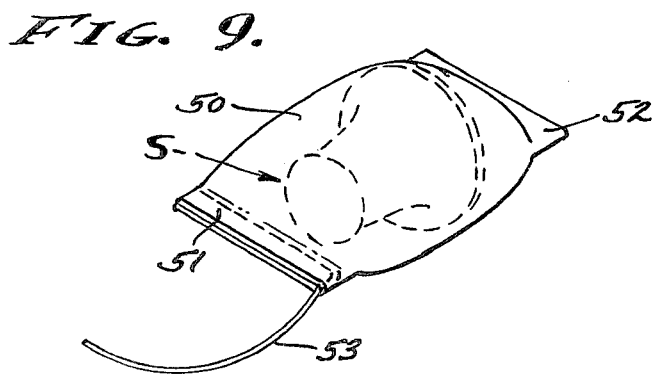

EYE MEDICATION DISPENSING FRAMES AND INSERT

BACKGROUND

The human eye is the organ of sight or vision, a substantially durable globe or ball that is moveable in the orbit or socket. Protection for the eye is provided for in the lids and lashes, and which are very sensitive and subject to involuntary or reflex action when the eye is disturbed by the approach or touching of foreign objects. Consequently the administering of medication to the eye can be difficult, and especially for those who are muscularly afflicted, simply aged, or in any way incapacitated in a manner to affect dexterity and/or equilibrium. Generally it is difficult for any person to administer medication to his own eyes, and particularly those persons who are incapacitated in a manner to adversely affect dexterity. Furthermore, the juxtapositioning of any object very close to the eye creates a condition wherein the person so administering said object cannot accurately judge position, and as a consequence the administering of liquid medication is often misdirected and thereby wasted as by washing away over the person's face. It is the use of squeeze-type eyedropper bottles for the application of medication with which this invention is concerned, namely any liquid medication that might be prescribed by an Oculist for the treatment of eye abnormalities and disease. It is, therefore, a general object of this invention to provide a therapeutic frame for self-administration of medication to the eyes, as may be prescribed by an Oculist. Although trained technicians can make the adjustments to the Oculists' prescription, it is a primary object herein for the individual person to adjust and fix the positioning of liquid application to suit the separate eyes. Further, this properly adjusted frame is adapted to be tamperproof and cannot later be maladjusted by those who are inexperienced in the anatomy of the eye. However, it is also feasible to retain adjustability of this frame for trial and/or later re-adjustment as circumstances require.

The usual optical frames are provided for mounting a pair of lenses before the eyes respectively. These frames are comprised of a bridge positioned over the person's nose, and a pair of laterally spaced rims supported by the bridge and held positioned to the person's brow by means of temples that extend therefrom to embrace the person's head over the ears. It is a frame such as this which is employed herein in combination with planar positioning means for the prescribed placement of an applicator guide to apply medication to the eye. For example, in the treatment of glaucoma, characterized by increased tension within and hardening of the eyeball, liquid medication is applied to the cornea as directly as possible; and not by indirection as might occur by flooding the eye from the corners thereof or for another example a general infection of the conjunctiva prefers flooding of the eye, in which case the eye is focused onto a lateral target so as to expose said conjunctiva.

Certain medication could irritate the cornea! Therefore, it is an object of this invention to provide positioning means by which a prescribed placement of medication can be made according to an individual's anatomy, and target means by which the eye is revolved so as to expose the desired portion of the conjunctiva. For instance, the inter-pupillary distance varies from person to person, and so does the height thereof with respect to the facial features; and there is of course asymmetry to be contended with. In other words, fine adjustments are to be made. Therefore, it is an object of this invention to provide for both inter-pupillary and height positioning of the aforesaid positioning means.

The transmission of light to the eye is a normal condition therefor, in order for a person to observe what is before him; darkness being detrimental. Therefore it is an object herein to provide for the transmission of light to the sensitive membranes of the eye, both for normal control of the iris and for vision, even though obstructed by the positioning means centered, for example, with the pupil in each instance. Accordingly, those members of this device which are disposed before the eyes are made of transparent material, all of which is conducive to cleanliness since smears are thereby easily detected and removed.

Inter-pupillary and height adjustment of guides as hereinabove referred to is to be retained, it being an object of this invention to provide friction lock means therefor. In carrying out this invention there is a common guide for both lateral and vertical adjustment, the guide being moveable within boundaries limited by a cam-shaped opening in the lens which carries the same. As stated above, the guides are transparent members, adjustably secured by the friction lock means and adapted to be permanently secured by the application of solvent when required.

It is an object of this invention to cooperatively combine the aforesaid guides and lock means into one simple device; the lock means being a tubular clamp adapted to receive a protective sleeve that positions the dispensing tip of the squeeze-type eyedropper bottle. The protection sleeve is an expendible member applied in a sanitary manner, as will be described. With the position determined by adjustment, the clamp means are operated to secure the guides. When absolute fixation is a requirement, solvent is applied between the (plastic) guides and lenses to fuse the same together in position.

It is an object of this invention to provide a system for self application of medication to the cornea or conjunctiva of the eye. Central focus of the eyes toward the eyedropper tip at the guide and sleeve openings is most natural, in which case the medication can be dropped by gravity onto the cornea. Additionally with the present invention, a target is visably exposed at the perimeter of the guide and carried by the guide into adjusted angular relation to the eye. Accordingly, focus of the eye onto the angularly related target disposed laterally of the normal axis of forward vision exposes a greater portion of the conjunctiva at one side of the eyeball. The guide is adjustably rotatable for this purpose.

It is an object of this invention to provide an aseptic system for self application of medication to the eye. In the administration of eyedrops it is a primary object to allow the medication to drop directly onto the eyeball without touching the surrounding tissue and without touching the eyedropper applicator to any foreign objects that would cause cross contamination. It is an eyedropper and preferably a squeeze-type eyedropper bottle with which this invention is concerned; a bottle with an integral eyedropper projection from a neck to which a protective closure is secured frictionally or by means of a threaded connection. In this way the eyedropper can remain sterile, provided that it does not contact other contaminating objects. Accordingly, I provide the sleeve for positioning the eyedropper in the guide carried by the lens in a frame that resembles a pair of eyeglasses. In accordance with this invention, the sleeve or sleeves are sterilized and they are expendable, and capable of being dispensed in a manner so that they are never touched directly by the person handling the same, and so that the eyedropper engaging parts thereof are not contaminated. In practice, the sleeves are supplied in openable envelopes of supple material from which they are manipulated and snapped into working position in the guide, in each instance. After use, the sleeves are snapped out of the guides and discarded, the closure being reapplied to the squeeze bottle to protect the eyedropper part thereof for subsequent use.

It is also an object of this invention to provide an inexpensive and yet practical kit for the proper positioning of an eyedropper for the dispensing of medicaments to the eye, directly therefrom. A container is provided for the transport of a frame that is preferably in the form of a folding eyeglasses, there being a compartment of the container that carries a squeeze-type eyedropper bottle. Additionally, there is the accommodation of sleeves that are dispensed in sterilized condition, for snapped engagement into the frame to receive and position the eyedropper. In other words, the kit provides the medication that is dispensed directly from the eyedropper which can be sterilized, without contamination by handling in the process of making ready for the application of said medication.

The foregoing and other various objects and features of this invention will be apparent and fully understood from the following detailed description of the typical preferred form and application thereof, throughout which description reference is made to the accompanying drawings.

DESCRIPTION OF THE DRAWINGS

FIG. 1 is a perspective view of the eye medication kit that is provided, and comprised of a compartmented compact that accommodates a folded eyeglass frame, a medication eyedropper bottle, and a supply of sterile inserts.

FIG. 2 is an enlarged perspective view of the expendable insert.

FIG. 3 is a side view of the squeeze-type eyedropper bottle.

FIG. 4 is a back-side view of the unfolded eyeglass frame and the guides which characterize this invention.

FIG. 5 is a side view of the eyeglass frame taken as indicated by line 5—5 on FIG. 4.

FIGS. 6 and 7 are sectional views, each taken through a rim and the eyeglass lens, FIG. 6 showing the eyeball focused centrally toward the eyedropper, and FIG. 7 showing the eyeball focused laterally towards a target.

FIG. 8 is an enlarged exploded view showing the guide and insert relationship, and FIG. 9 is an enlarged perspective view showing the enveloped insert as it is supplied in sterile condition.

PREFERRED EMBODIMENT

It is a sensitive organ, the eye, with which this invention is concerned, providing a therapeutic frame for the Oculist to prescribe a positioning or for the person involved to determine proper positioning for the gravitational application of medication, for example directly onto the cornea or onto the conjunctiva. The eyeball is comprised of the segments of two dissimilar spheres. The segment of the lesser sphere forms the anterior part of the eye and is composed of a strong horn-like membrane, the cornea, within which are the aqueous humor and the iris capable of contraction and dilation of an opening, the pupil, normally centered for the transmission of light. The segment of the larger sphere forms the surrounding conjunctiva and the posterior part of the eye, and is composed of three layers, the sclerotic continuing from the cornea, the choroid continuing from the iris, and the retina which consists of a cup-like extension of the optical nerve. It is the former lesser sphere, the cornea, and the conjunctiva, with which this invention is particularly concerned and for which the frame and guides of the present invention are provided to serve in the care and healing of the eyes through the most advantageous application of medication as determined by medical science for the treatment thereof.

Referring now to the drawings, the frame of the present invention resembles a pair of eyeglasses in a frame F, with transparent lenses L and adjustment guides G and adjustment-lock means X for the selective positioning and fixation of the guides thereof which locates an eyedropper received thereby. A sleeve S snaps into each guide G so as to receive and position the eyedropper tip, as shown. The frame can be fabricated of any suitable material, preferably plastic, and is comprised of a pair of rims 10 joined by a bridge 11, and a pair of temples 12 extending rearwardly from the hinges 13 at each rim. The rims can vary in configuration and each forms a frontal window before the eye of the wearer. The rims are grooved to hold the lenses as later described. The bridge 11 is a horizontal member that rigidly joins the two rims 10 in laterally spaced relation with nose pieces 10'. In practice, the nose pieces 10' can be a separate part, or integral as shown, for adaptation to the person's nose. The hinges 13 are at opposite sides of the frame and extend rearwardly and outwardly, as shown. The temples 12 are bows that pivot from the hinges in the usual manner to embrace the head.

In carrying out this invention, there is a container C for the transport of the eyeglass frame F with its lenses L and ajustable guides G, together with a supply of sterile sleeves S and a squeeze-type eyedropper bottle B and its supply of medication to be dispensed. Conventional eyeglass frames F as above described can be employed, however it is preferred that folding eyeglass frames be used. Accordingly, the rims 10 are joined by an articulated bridge 11 connecting the rims with spaced pivots whereby the rims can collapse and lie flat one against the other with the bridge extending as a separate part therebetween. Stops are provided to limit the extended working position of the rims 10, as shown. Each temple 12 is broken into inner and outer sections and joined by an articulated link 14, whereby the two sections of the temple can fold flat against opposite sides of the rims with the links extending as separate parts therebetween. Stops are provided to limit the extended working positions of the temples 12, as shown. The temples 12 at opposite side rims of the frame F are offset to clear each other when folded.

A lens L is held in each rim 10 of the frame F, preferably a flat planar lens, although a concavo-covex lens is applicable with corresponding shape applied to the guide G, later described. In practice, the lenses L are darkened or smoked so as to substantially reduce or soften incoming light, and are made of transparent plastic material with a centrally located opening 15 adapted to pass the adjustment-lock means X with substantial clearance. A feature of this invention is the controlling cam-shape of the opening 15 limiting movement of the guide G and its adjustment-lock means X to practical limits and always within a range of use, without exposing the opening 15. In practice, greater latitude of movement is provided as the guide G and means X are moved inwardly and more restrictive when moved outwardly. Also, greater latitude downwardly than upwardly; all as circumstances require.

In accordance with this invention, I provide the guides G for the horizontal and vertical omni placement of the eyedropper 40 or the positioning sleeves S therefor. The guides G are alike at each right and left lens L, and each comprises inner and outer slides 20 and 21 of transparent material; characteristically of substantially greater extent than the area of the opening 15 in each instance, so as to overlap the perimeter of opening 15 in all instances. In practice, the slides are coextensive plastic plate-like elements of the same or different transparency from that of the lenses embraced thereby. A flat lens L has complementary flat slides 20 and 21, while a curved lens has complementary curved slides; all for sliding frictional engagement when manipulated into the placement required, whereby the center of the guide G is positioned in each instance as required.

The slides 20 and 21 of the guide G are interconnected by a tubular barrel 30 that extends therebetween and through the opening 15. The barrel 30 is cylindrical and its periphery has stopped engagement with the perimeter wall of the opening 15, and is free to move into an adjusted position. In FIGS. 6 and 7 of the drawings, the barrel 30 is integral with one inner slide 20 and is shouldered and secured to the other outer slide 21, one or both of the slides being initially dished inwardly so as to establish the required frictional engagement with the lens L (see FIG. 8). In FIG. 8 of the drawings, the barrel 30 is in an adjusted tension with respect to opposition of the two slides 20 and 21 against the lens L, in which case the guide-adjustment-lock means X is incorporated therein as next described.

In accordance with this invention, the guide-adjustment-lock means X is provided to tension the slides 20 and 21 against the lens L therebetween, thereby adjusting the frictional engagement for securing a position over a portion of the eyeball as required. The guide-adjustment-lock means X is comprised of the tubular barrel 30 slidably engaged through the opening 15, and a nut 31 threadedly engaged thereon. The barrel and nut are also made of transparent or translucent material integral with the slides 20 and 21, and formed so as to directly receive and to pass the eyedropper or sleeve S later described. The peripheries of the slides are knurled so that they can be manually rotated relative to each other and thereby to tighten or loosen the threaded engagement. Accordingly, the guide G comprising the two slides can be moved against adjusted friction, or said friction can be increased so as to be an effective lock against movement.

The tubular barrel 30 is adapted to directly receive the eyedropper 40, or as shown to receive the sterile sleeve S which in turn receives and passes the eyedropper 40 coaxially centered therethrough. The tip 41 of an eyedropper is tapered and of a standardized small diameter, extended from a nominally larger diameter body or neck 42 of the squeeze-type eyedropper bottle B. The bottle body 43 is depressible, in lieu of the bulb of an eyedropper per se, in order to provide pressure for dispensing medication in measured amount, and for loading when in eyedropper-bulb form. Accordingly, the barrel 30 has a funnel-shaped and tapered bore 32 restricted toward the eye, to freely pass the tip 41 a short distance and to stop the same and the body or neck 42 of the eyedropper or eyedropper bottle B; so that medication is applied direct from the eyedropper and so that the tip 41 is prevented from touching the eye per se (see FIGS. 6 and 7). The barrel 30 is positioned relative to the inner slide 20.

The target T is provided for rotating the eyeball into omni lateral positions that will expose a desired portion of the conjunctiva for application of medication thereto. As above described, the slide 20 is frictionally engaged with the inside of the lens L and is therefore revolvable through manual engagement with the knurled periphery or target projection thereof. In accordance with this invention, a spot or opening of distinguishable character is placed at the peripheral margin of the slide which is circular, and preferably a round dot 48 of bright paint or the like, such as Scotch-Lite as manufactured by 3-M Company. By revolving the slide 20 a laterally displaced positioning of the dot 48 is established and which can be focused upon by the eye in order to turn the eyeball into a direction that will expose a greater than normal portion of the conjunctiva for the application of medication thereto. This target positioning avoids reflex blinking action of the eyes, since the medication drops are not in the line of vision (see FIG. 7).

In accordance with this invention, there are expendable sleeves S supplied in sterilized condition, to be received in the tapered bores 32 of the guides G and in turn to protectively receive and position the eyedropper 40. A feature is that the sleeves snap into working position to be removably positioned in the guides. In practice, the inner side of slide 20 is chamfered at 44 so as to receive a projecting peripheral rib 45 at the inner extremity of the sleeve, the sleeve being slotted at 46 to permit inward depression of the rib for entry and to facilitate release. The exterior of the sleeve is complementary to the taper of bore 32 to have a stopped position when held secure by the rib 45, and has a manually engageable lip 47 displaced from the outer side of slide 21 when in its working position. As shown, the sleeve S is made of thin walled plastic or the like, such as Nylon as manufactured by DuPont, that is easily made by means of injection molding and which can be readily sterilized. This sleeve S is made in quantity and is an expendable part to be discarded after use.

The sleeves S are stored in sterilized condition by means of enveloping them in openable bags 50 of supple plastic material. Form-and-fill packaging can be empolyed, wherein a continuous tube of supple plastic film is formed to pass over individual sleeves S and hermetically sealed at each end 51 and 52 of the tube so as to isolate the individual sleeve S from the surrounding environment. In practice, a tear line or tear strip 53 is provided to facilitate opening of the bag 50 at the inner end of the sleeve S, whereby said sleeve can be easily manipulated from the bag 50 and into the tapered opening 32 and pressed into snapped engagement with the guide, all without touching the sleeve. The dispensing squeeze-type eyedropper bottle B is then opened by removal of the protecting closure, and without touching the eyedropper 40 it is entered into the sleeve S and guided into working position as above described.

In carrying out this invention and as best illustrated in FIG. 1 of the drawings, the frame F, insert sleeves S and squeeze-type eyedropper bottle B with its supply of medication are altogether made available in kit form. Accordingly, there is the container C that is compartmented to accommodate the aforesaid items F, S and B in a "compact" form having a compartmented base 60, with a center compartment a providing fitted accommodation for the folded eyeglass frame F, with one end compartment b providing fitted accommodation for the renewable squeeze-type eyedropper bottle B, and with the other end compartment c providing a bin for the accommodation of a multiplicity of bags 50 enveloping the sterilized sleeves S. A removable cover 61 closes the container.

From the foregoing, it will be seen that this therapeutic device can be easily manufactured, preferably of injection molded plastic, assembled by pinning the rims 10 and temples 12 together, after which the guides G are passed through the openings 15 in each instance. The frame assembled as thus described is then fitted to the person or by the person who is thereafter to administer medication to their own eye or eyes by means of inserting the sterile sleeves into the bores 32 for the reception of an eyedropper 40. An alternate to the pinned frame is an injection molded polypropylene frame with integral hinge membrane. The frame is fitted to the head and features of the person, followed by selective positioning of the guides G dependent upon the posture to be taken by the person who is to administer the drops of medication, it being recognized, for example, that there will be different alignments required for a person merely tilting his head back as compared with a person who is lying down. In any case, the friction of the slides 20 and 21 is adjusted as may be desired and the guides G moved into the required alignment for accommodating inter-pupillary distance, the guide-adjustment-lock means X is tightened when employed, and the target T is utilized when a certain portion of the conjunctiva is to be exposed. It is to be understood that the application of medication is by gravitation for deposit upon a specified area of the eye.

Having described only a typical preferred form and application of my invention, I do not wish to be limited or restricted to the specific details herein set forth, but wish to reserve to myself any modifications or variations that may appear to those skilled in the art as set forth within the limits of the following claims.

I claim:

1. A therapeutic frame for adiministering liquids by gravity from an eyedropper and onto a selective area of a person's eyeball, and including; a frame comprised of a nose bridge carrying spaced rims for disposition over the eyes of the person, at least one of said rims carrying a lens with a central opening therethrough and a shiftable guide comprised of inner and outer slides and a barrel passing through said opening with restricted lateral clearance with the inner and outer slides frictionally embracing the lens for adjustable lateral positioning with respect to the rim, there being a bore through the barrel of the guide to receive and locate the eyedropper over an area of the person's eyeball where medication is to be applied.

2. The therapeutic frame for administering liquids to the eyeball as set forth in claim 1, wherein the inner slide is rotatable and has a peripheral target to be viewed by the eye and for selective lateral positioning and turning of the cornea of the eyeball away from the position of the eyedropper while exposing the conjunctiva thereto.

3. The therapeutic frame for administering liquids to the eyeball as set forth in claim 1, wherein the lens is transparent for the admission of light to the eye.

4. The therapeutic frame for administering liquids to the eyeball as set forth in claim 1, wherein the lens and guide are transparent for the admission of light to the eye.

5. The therapeutic frame for administering liquids to the eyeball as set forth in claim 1, wherein the lens is of light restricting material for the controlled admission of light to the eye.

6. The therapeutic frame for administering liquids to the eyeball as set forth in claim 1, wherein the lens is of light restricting material for the reduction of incoming light and the guide slides are of light restricting material establishing a visibly darkened target area before the eye.

7. The therapeutic frame for administering liquids to the eyeball as set forth in claim 1, wherein the periphery of the lens opening is cam-shaped to limitedly control the extent of lateral adjustment of the guide.

8. The therapeutic frame for administering liquids to the eyeball as set forth in claim 1, wherein the peripheries of the guide slides extend laterally over the perimeter of the opening through the lens.

9. The therapeutic frame for administering liquids to the eyeball as set forth in claim 1, wherein a periphery of the lens opening is enlarged inwardly toward the nose bridge and is more restrictive outwardly to limitedly control the extent of lateral alignment of the guide.

10. The therapeutic frame for administering liquids to the eyeball as set forth in claim 1, wherein the guide slides are inwardly dished for pressured engagement against opposite sides of the lens and with peripheries of the slides laterally over the perimeter of the opening for frictional engagement with the lens.

11. The therapeutic frame for administering liquids to the eyeball as set forth in claim 1, wherein the barrel of the guide is threaded to at least one of the slides for adjusted pressured engagement against opposite sides of the lens and with peripheries of the slides extended laterally over the perimeter of the opening for frictional engagement with the lens.

12. The therapeutic frame for administering liquids to the eyeball as set forth in claim 1, wherein the guide slides are inwardly dished against the lens and the barrel of the guide and threaded to at least one of the slides for adjusted pressured engagement against opposite sides of the lens and with peripheries of the slides extended laterally over the perimeter of the opening for frictional engagement with the lens.

13. The therapeutic frame for administering liquids to the eyeball as set forth in claim 1, wherein an expendable sleeve is replaceably insertable into the bore through the barrel of the guide to receive and locate the eyedropper.

14. The therapeutic frame for administering liquids to the eyeball as set forth in claim 1, wherein an expendable sleeve with a depressible rib engageable through and into position in a chamfer of the bore through the barrel is replaceably insertable therein to receive and locate the eyedropper.

15. The therapeutic frame for administering liquids to the eyeball as set forth in claim 1, wherein a sterile sleeve is stored in an openable envelope from which it is manipulatable without touching and replaceably insertable into the bore through the barrel of the guide to receive and locate the eyedropper.

16. The therapeutic frame for administering liquids to the eyeball as set forth in claim 1, wherein a sterile sleeve with a depressible rib engageable through and into position in a chamfer of the bore through the barrel is stored in an openable envelope from which it is manipulatable without touching and replaceably insertable into the bore through the barrel of the guide to receive and locate the eyedropper.

* * * * *